(12) United States Patent
Lee

(10) Patent No.: US 7,434,990 B2
(45) Date of Patent: Oct. 14, 2008

(54) METHOD TO DETECT TERMITE INFESTATION IN A STRUCTURE

(75) Inventor: Peng Lee, Oxford, MS (US)

(73) Assignee: University of Mississippi, University, MS (US)

( * ) Notice: Subject to any disclaimer, the term of this patent is extended or adjusted under 35 U.S.C. 154(b) by 57 days.

(21) Appl. No.: 10/711,248

(22) Filed: Sep. 3, 2004

(65) Prior Publication Data
US 2005/0018745 A1    Jan. 27, 2005

Related U.S. Application Data

(63) Continuation-in-part of application No. 10/680,377, filed on Oct. 7, 2003, now Pat. No. 7,271,706, and a continuation-in-part of application No. 10/708,571, filed on Mar. 11, 2004.

(60) Provisional application No. 60/417,257, filed on Oct. 9, 2002.

(51) Int. Cl.
*G01N 25/00* (2006.01)
*G01J 5/00* (2006.01)

(52) U.S. Cl. ............... 374/121; 374/4; 374/7; 374/45

(58) Field of Classification Search ........... 374/45, 374/4, 5, 121, 7; 43/132.1; 250/341.1
See application file for complete search history.

(56) References Cited

U.S. PATENT DOCUMENTS

| | | | |
|---|---|---|---|
| 3,791,097 A | 2/1974 | Cassella et al. ........ 52/741 |
| 4,495,518 A * | 1/1985 | Sanoian ............... 348/164 |
| 4,550,376 A | 10/1985 | Maciejczak ........... 364/512 |
| 4,647,220 A | 3/1987 | Adams et al. ............ 374/5 |
| 4,768,158 A | 8/1988 | Osanai ................ 364/507 |
| 4,809,554 A | 3/1989 | Shade et al. |
| 4,941,356 A | 7/1990 | Pallaske ............... 73/587 |
| 5,285,688 A | 2/1994 | Robbins et al. ......... 73/587 |
| 5,444,241 A | 8/1995 | Del Grande et al. .... 250/253 |
| 5,571,967 A | 11/1996 | Tanaka et al. .......... 73/587 |
| 5,592,774 A | 1/1997 | Galyon ................. 43/124 |
| 5,631,465 A | 5/1997 | Shepard .............. 250/330 |
| 5,637,871 A | 6/1997 | Piety et al. ........... 250/330 |
| 5,719,395 A | 2/1998 | Lesniak .............. 250/330 |

(Continued)

FOREIGN PATENT DOCUMENTS

JP    H07-143837    6/1995

(Continued)

OTHER PUBLICATIONS

James et al., "Finding Termites With Thermal Imaging Cameras", Aug. 1, 2002, Termicam Pty Ltd., Melbourne, Australia.*

(Continued)

*Primary Examiner*—Gail Verbitsky
*Assistant Examiner*—Mirellys Jagan
(74) *Attorney, Agent, or Firm*—Baker, Donelson, Bearman, Caldwell & Berkowitz, PC

(57) ABSTRACT

A method for confirming the presence of termites in a structure, involving a preliminary infrared scan of a structure and confirmation of termite infestation with at least one detector in order to quickly locate potential areas of termite infestation.

8 Claims, 4 Drawing Sheets

U.S. PATENT DOCUMENTS

| | | | |
|---|---|---|---|
| 5,742,335 A | 4/1998 | Cannon | 348/135 |
| 5,815,090 A | 9/1998 | Su | 340/870.16 |
| 5,834,661 A | 11/1998 | Nonaka et al. | 73/866 |
| 5,877,422 A | 3/1999 | Otomo | 73/587 |
| 5,886,636 A * | 3/1999 | Toomey | 340/602 |
| 6,028,625 A | 2/2000 | Cannon | 348/135 |
| 6,052,066 A | 4/2000 | Su | 340/870.1 |
| 6,081,481 A | 6/2000 | Sabatier et al. | 367/8 |
| 6,150,944 A | 11/2000 | Martin et al. | 340/632 |
| 6,166,641 A * | 12/2000 | Oguchi et al. | 340/573.1 |
| 6,192,325 B1 | 2/2001 | Piety et al. | 702/184 |
| 6,313,643 B1 * | 11/2001 | Tirkel et al. | 324/642 |
| 6,516,084 B2 | 2/2003 | Shepard | 382/141 |
| 6,714,017 B2 | 3/2004 | Enachescu et al. | 324/501 |
| 6,751,342 B2 | 6/2004 | Shepard | 382/141 |
| 7,271,706 B2 | 9/2007 | Lee | |
| 2001/0001851 A1 | 5/2001 | Piety et al. | 702/184 |
| 2002/0096638 A1 * | 7/2002 | Toomey | 250/341.1 |
| 2003/0039612 A1 * | 2/2003 | Ovington | 424/9.1 |
| 2003/0146840 A1 * | 8/2003 | Donskoy et al. | 340/573.2 |
| 2003/0230717 A1 | 12/2003 | Reilly et al. | 250/341.6 |
| 2004/0162710 A1 | 8/2004 | Schwartz | 703/2 |
| 2005/0212691 A1 * | 9/2005 | Tirkel et al. | 342/22 |
| 2007/0096928 A1 | 5/2007 | Lee | |
| 2007/0198226 A1 | 8/2007 | Lee | |

FOREIGN PATENT DOCUMENTS

| JP | H07-255344 | 9/1995 |
|---|---|---|

OTHER PUBLICATIONS

U.S. Appl. No. 11/893,240, Lee.
U.S. Appl. No. 11/940,093, Lee.
Thermal Inspection services (http://www.thermalinspections.com) "Residential Inspections" New Home Inspections.
"Infrared Building Science" Infrared Training Center.
"SBA Thermographics" Infrared Thermography Jul. 21, 2001.
Infrared Thermography http://www.maverickinspection.com/inelectapp.html) Maverick.
Infrared Thermography http://www.maverickinspections.com.
U.S. Appl. No. 10/680,377, Lee et al.
U.S. Appl. No. 10/708,571, Lee et al.
Mark Gilbert, Thermal Imaging Puts Termite in the Red, National Center for Preservation Technology and Training, Nov. 2001.
Jan Suszkin, Taking Aim at Formosan Subterranean Termites, Agricultural Research, Oct. 2000, vol. 48, No. 10, p. 12-15.
David Rice, General Thermography, Snell Infrared Message-boards, Nov. 8, 2000.
Amy Spillman, Operation Full Stop: Stopping the Swarm, Agricultural Research, Jul. 2003—vol. 51 No. 7, p. 4-8.
USDA Agricultural Research Service, 2004 Annual Report.
John Snell, Thermographic Applications, Snell Infrared Messageboards, Jul. 22, 2002, USA.
National Park Service, FY2004 Budget Justifications, Activity: Cultural Programs, p. NRP-30-44, FY 2002 p. 37.
Jon L Grossman, IR Thermography as a Tool for the Pest Management Professional, IR Info 2004 Proceedings Paper.
Ken James, Finding Termites with thermal Imaging, Infra Motion 2002, Sep. 29-Oct. 2, 2002 Orlando, FL.
Bill Craft, Re: Locate hidden termite damage, Snell Infrared Messageboards, Dec. 27, 1997.

* cited by examiner

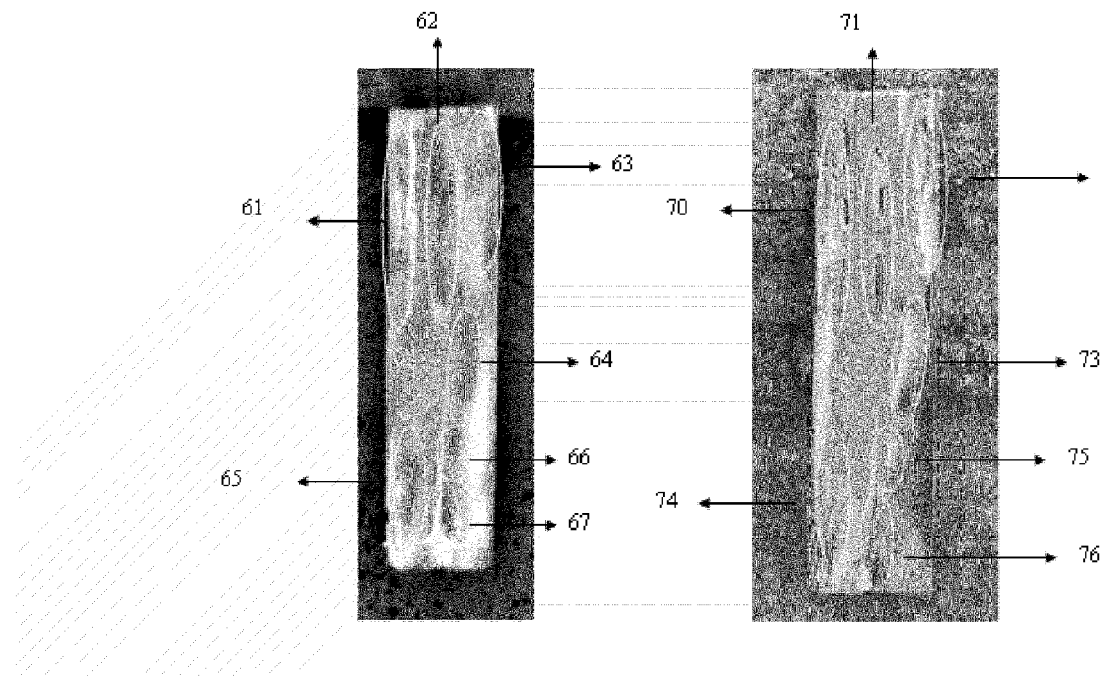
FIGURE 3A　　　FIGURE 3B

METHOD TO DETECT TERMITE INFESTATION IN A STRUCTURE

CROSS REFERENCE TO RELATED APPLICATIONS

This application is a continuation-in-part and claims the benefit under 35 U.S.C. § 120 of U.S. application Ser. No. 10/680,377 filed Oct. 7, 2003 and U.S. application Ser. No. 10/708,571 filed Mar. 11, 2004, and 35 U.S.C. § 119(e) of U.S. Provisional Application Ser. No. 60/417,257 filed Oct. 9, 2002, hereby specifically incorporated by reference in their entirety.

STATEMENT REGARDING FEDERALLY SPONSORED RESEARCH OR DEVELOPMENT

U.S. Department of Agriculture Award # 58-6402-04-040

BACKGROUND OF THE INVENTION

This invention relates to nondestructive detection of termite infestation in a structure and, more particularly, to methods for detecting and preventing termite damage.

SUMMARY OF THE INVENTION

Termites are extremely destructive to wood material. Termites attack and destroy wood almost everywhere in the world, with the exception of climate zones that experience hard freezing. There are close to fifty species of termites in the United States, the majority of losses to wood material being caused by subterranean species. All termites are social insects. They live in colonies that can number over one million individuals.

It is difficult to put a dollar amount estimate on termite damage. However, renowned termite scientist Dr. Nan Yao Su at the University of Florida has estimated that the total annual cost of termite control and damage repair for the United States alone was $11 billion in 1999.

Few homes are treated for termite detection/prevention during construction, although this is the best and most economical way to prevent termite attack. Untreated foundations make the house very susceptible to termite attack. It is often very difficult and costly to apply effective control measures after a building has become infested with termites.

It is rarely apparent from visual observation that a termite infestation is active and that wood damage is occurring. Typically, only about 30 percent of structural wood in a structure is visible for visual inspection. Even when visible wood is to be inspected, an inspector often has to rely on secondary signs of an infestation, such as moisture staining, the presence of foraging tubes and debris expelled from termite colonies.

Another method often used to detect termites is to tap the surface of the wood while listening for a characteristic sound indicative of an underlying gallery void. When a suspected area is located, the inspector applies a sharp probe, such as a screwdriver, to break the wood surface and locate wood galleries and live termites. This method has significant disadvantages. The confirmation of an active infestation requires some localized damage to the wood. Also, when termites are exposed in this manner, the destruction induces termites to retreat from the disturbed area and may reduce the effectiveness of a subsequent localized treatment.

Commercial demand for a dependable, nondestructive and nonsubjective method to detect termites has spawned a number of alternatives to visual inspection. However, none of these techniques has satisfied the non-destructive and non-subjective requirements, and many infestations are still missed.

Prior devices for nondestructive detection of termites may be generally classified into four categories: (1) Apparatus having sensors that detect the presence of gases emitted by termites, as disclosed for example in U.S. Pat. No. 6,150,944; (2) Apparatus having acoustic sensors that detect insect sounds at high or ultrasonic frequencies, as disclosed for example in U.S. Pat. No. 4,809,554 to Shade et al., U.S. Pat. No. 5,285,688 to Robbins et al., and Japanese Patent Application JP H07-143837; (3) Apparatus having sensors that detect destruction of a baited sample, for example, inclusion of circuit elements designed to be destroyed as the sample is destroyed, thereby breaking a circuit, as disclosed in U.S. Pat. Nos. 6,052,066; 5,815,090; 5,592,774; activation of a switch by movement of a mechanical element in response to sample destruction, as disclosed in U.S. Pat. No. 5,571,967 and Japanese Patent Publication No. H7-255344; or penetration of a film across the entrance to a baited trap, as disclosed in U.S. Pat. No. 5,877,422; and (4) Apparatus employing infrared sensors.

Detection devices that rely on sensing the presence of termite-created gases eliminate the need to use bait to attract the termites, and, in theory, they can signal the actual locations of the termites. A significant disadvantage, however, is that the gases must be abstracted within a confined space, such as within the walls of a structure. These devices are thus unsuitable for detecting termites in wood that is not within a confined space. Moreover, the use of these devices to detect termites is very time-consuming and costly as a result.

Detection devises that rely on sensing ultrasonic termite sounds, on the other hand, offer the advantage that they can be placed on the exterior of structural walls rather than within the walls. The ultrasonic frequencies, however, are difficult to detect through walls and other concealing structures due to the signal's very short distance of travel (ultrasonic frequencies have very high transmission loss), and this process fails to take into account the full range of termites noises, which fall primarily in the range of 100 Hz to 15 kHz.

An alternative to devices employing ultrasonic acoustic sensors is a device employing sensor (or electronic stethoscope) arranged to detect acoustic signals and process them for listening and directs interpretation by a trained operator. In some cases, the device may be connected to a spectrum analyzer arranged to generate a plot of signals in the frequency domain, which can then be interpreted by the operator. These devices require a high degree of operator skill. In addition, such devices typically use a relatively narrow frequency range. For example, the device disclosed in U.S. Pat. No. 4,895,025 is focused on a frequency range of 1462.5 Hz to 3337.5 Hz. The device of U.S. Pat. No. 4,941,356 (the '356 patent), on the other hand, is evidently intended to work over a broad range of audible frequencies (100 Hz to 15 kHz). The "356 patent, however, fails to disclose specific apparatus, algorithms or noise patterns useful for detection over the specified frequency range.

The various devices for sensing the destruction of bait sample are useful for detecting the presence of termites in the vicinity of a structure, but cannot be used to locate precise areas of termite infestation in concealed areas within the structure. Once it has been determined that termites are present in the vicinity of the structure, the only way to determine the actual locations of termites within the structure is to remove portions of the structure, which is, again, damaging and costly.

It has also been proposed to use infrared sensors to detect the surface temperature differences indicative of termite infestations. Infrared detection works because subterranean termites require a high percentage of humidity in their living environment. Moisture brought in by the termites produce a temperature change in the wall, which can be detected by an infrared thermal imaging device. However, this is a relatively nonspecific method, yielding many, many false positives since there are many sources of temperature differences in a typical structure, such as non-uniform insulation material, air-conditioning ducts, leakage, air movement through wall cracks, water and moisture problems, etc. As a result, detection of termites using infrared sensors still requires destruction of walls to verify results and to more specifically locate the actual termite infestations. Furthermore, use of infrared sensing for detection of termites also requires a relatively high degree of operator skill, training and judgment which adds time and cost to its use.

Devices relying on acoustic detection appear to offer the best combination of accuracy and lack of destruction. Such devices, however, generally do not take into account the full range of termite sounds, as explained above. Moreover, the design of prior devices has generally resulted in only highly localized detection ability, thereby necessitating the taking of many samples or data points, and requiring an inordinate amount of time or number of sensors to completely inspect a structure.

As a result of the various practical difficulties outlined above, the prior devices described above have generally seen insignificant commercial implementation despite the long-felt need for nondestructive termite and wood-destroying insect detection. There is still a need for a nondestructive, reliable and easy-to-use apparatus and method for detecting termites.

The present invention relates to a method to detect termite infestation. In particular, an infrared scan of a structure is conducted to identify potential infestation sites. Then once potential infestation sites are identified, another nondestructive detection method such as a microwave is used to confirm termite infestation in the structure.

Preliminary infrared detection has the advantage of covering a much larger area than acoustic detection and, although less specific or accurate than acoustic detection, provides efficient screening and a convenient way of scanning the structure for potential infestations in order to guide placement of detectors in order to carry out more specific tests. In this way, inspection time requirements, and, therefore, costs, are greatly reduced. Further, detection accuracy is greatly increased. The combination of infrared and other detection method couples a quicker but low-specificity screening technique for speed with a high-specificity, slower technique for accuracy and is a significant improvement in the art having important commercial applications.

BRIEF DESCRIPTION OF THE DRAWINGS

FIG. 3A is an infrared scan of a structure showing drywood termite infestation.

FIG. 3B is a photo of a wood structure with the surface material removed.

DETAILED DESCRIPTION

Figure 1:
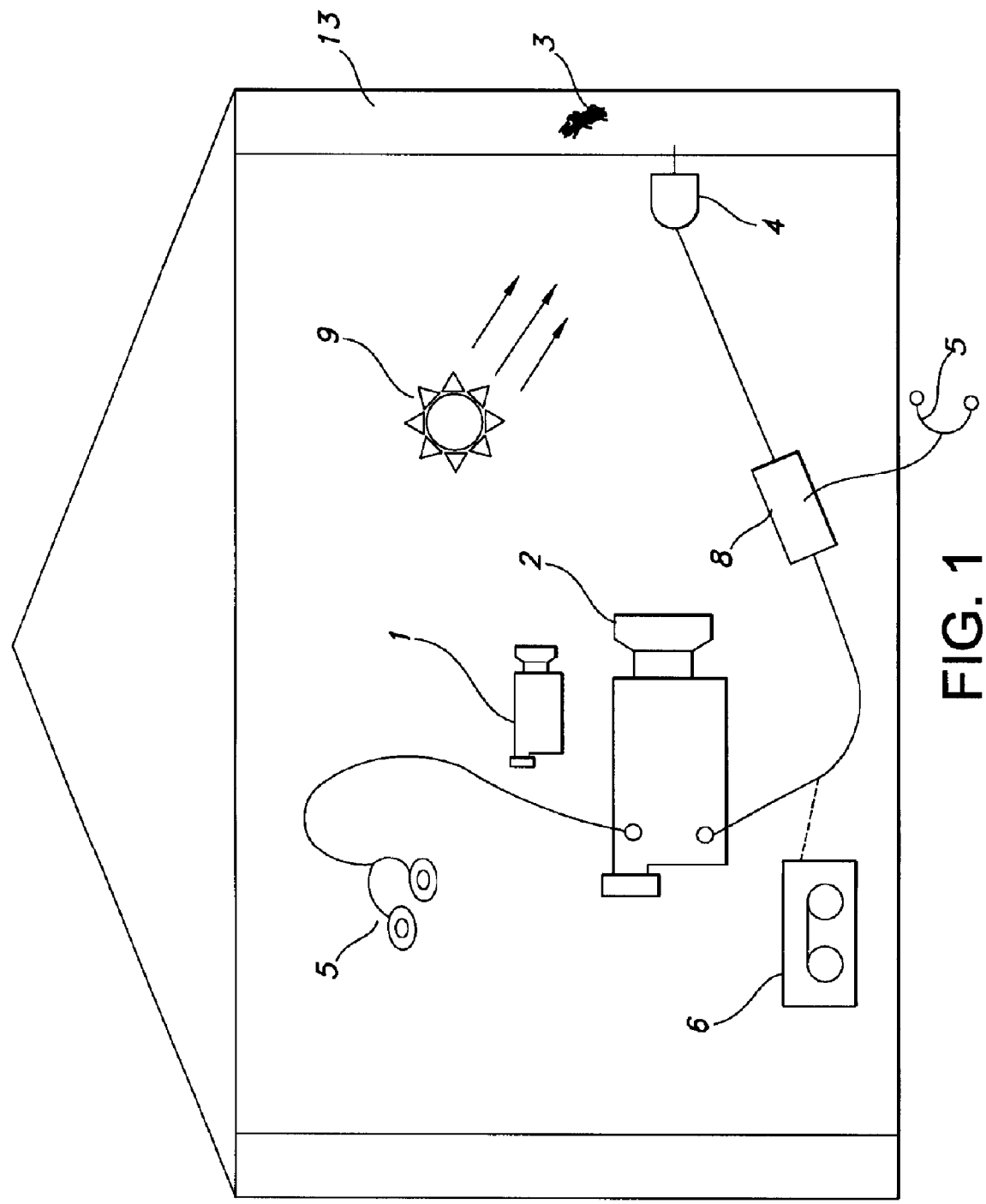
FIG. 1 is a schematic illustration of a termite detection system assembled in accordance with the principles of a preferred embodiment of the invention.

As schematically depicted in FIG. 1, a preferred embodiment of the apparatus and method of the present invention includes a thermal imaging camera 1 for performing a preliminary scan of a structure 13 in order to locate potential termite infestations sites 3. A thermal imaging camera 1 is used to perform an infrared scan. The structure 13 can be a wooden object, such as a wall stud, paneling or in one embodiment a live tree. Termite infestation sites 3 can be the result of subterranean termite or dry-wood termite activity. In the case of a subterranean termite infestation, the moisture brought in by the subterranean termites will show up as a "suspicious cold or hot spot" in a thermal imaging scan. In the case of a dry-wood termite infestation, a heat or cold source 9 is needed to increase or decrease the temperature of a targeted structure 13. This heat source 9 can be an electric, gas or oil heat source as well as an incandescent or infrared light source. The areas in the targeted structure 13 that contain a cavity created by dry-wood termites will show up as "suspicious warm or hot spots." The correspondent video images of the potential termite infestation are recorded by the camcorder 2 or by the thermal imaging camera if it is equipped with recording capability 6.

Thermal imaging camera 1 may be any of a number known, commercially available infrared cameras conventionally used by structural engineers, police and the military. In order to improve the accuracy by which the thermal imaging camera 1 detects potential areas of termite infestation, the thermal imaging camera may further include termite infestation recognition software, such as matched filtering software which compares the frequency spectrum of a thermal image with frequency spectra of a reference images known to indicate termite infestation, thereby reducing the level of skill required of the camera operator, reducing time required and increasing termite identification effectiveness. This database of infestation images of suspicious thermal images can be built by one skilled in the art.

Specific equipment to facilitate an infrared scan of a structure and procedures to enhance the resolution of the scan are described in U.S. patent application Ser. No 10/708,571.

Figure 2A:
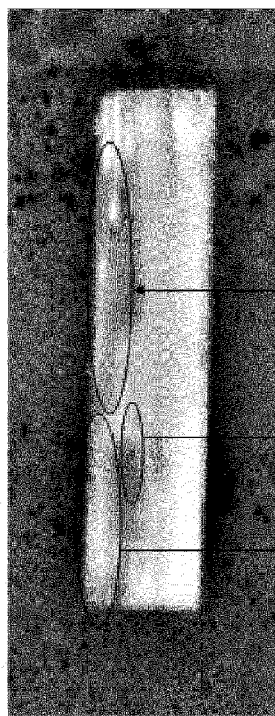
FIG. 2A is an infrared scan of a structure showing drywood termite infestation.
Figure 2B:
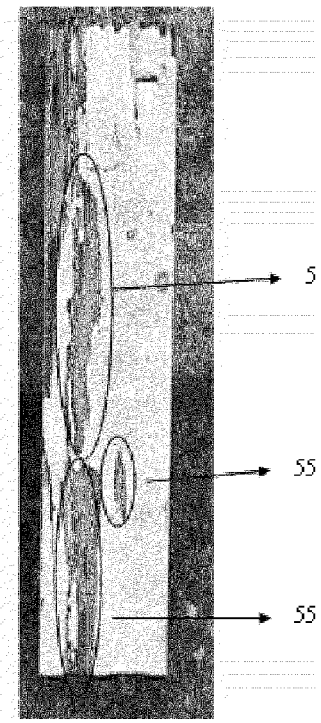
FIG. 2B is a photo of a wood structure with the surface material removed.

Referring now to FIGS. 2A and 2B, an infrared scan of a wall shows potential termite damage at 50, 51 and 52. The surface material was removed in FIG. 2B to show termite damage at 53, 54 and 55.

Referring now to FIGS. 3A and 3B, an infrared scan of a wall shows potential drywood termite damage at 61-67. The surface material was removed in FIG. 2B to show termite damage at 70-76.

Figure 4A:
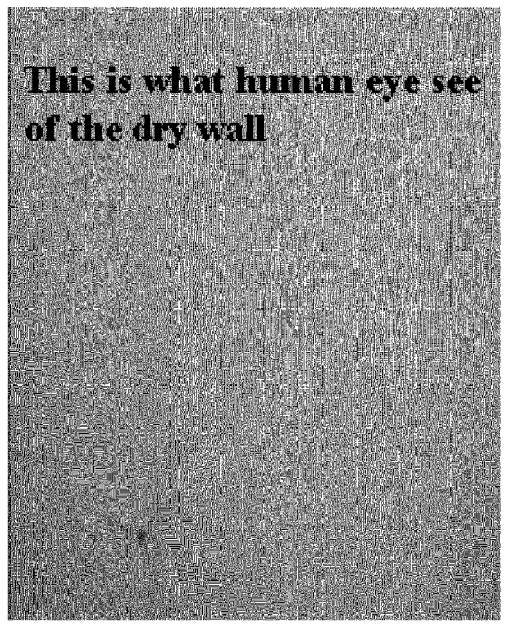
FIG. 4A is a photograph of a wall.
Figure 4B:
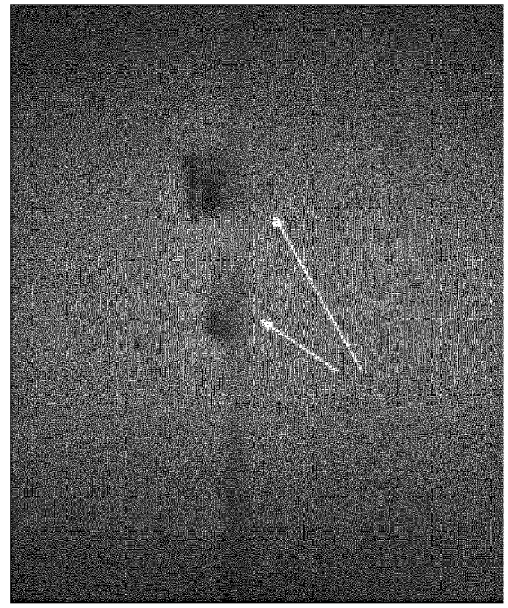
FIG. 4B is an infrared scan of the wall.
Figure 4C:
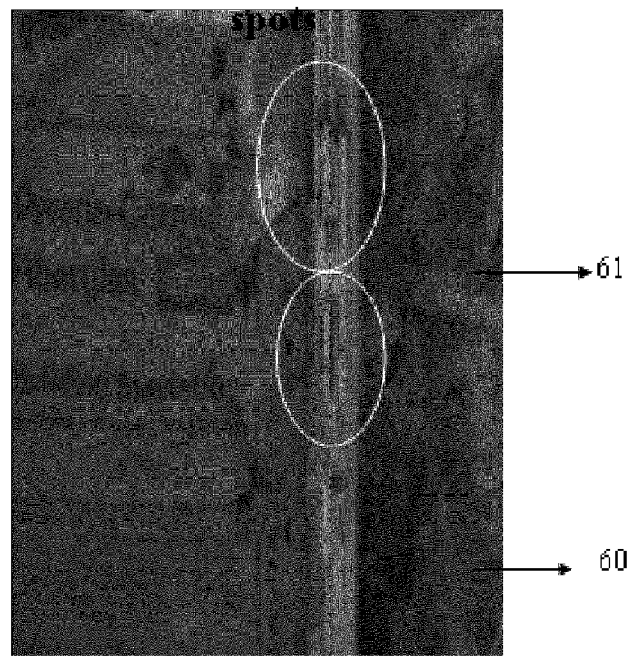
FIG. 4C is a photograph of the wall with the dry wall removed, it shows the 2×4 stud damaged by subterrarean termite.

FIG. 4A-4C show additional preliminary infrared detection. In FIG. 4A, a photograph of a wall is shown. This is what a human eye sees. In FIG. 4B, a preliminary infrared scan shows suspicious black spots which might be subterranean termite infestation. Subterranean termite infested areas contain very high moisture content, as the moisture evaporates infested areas appear as cold spots. In FIG. 4B, when the wall is removed, actual termite damage is shown at 60 and 61. However, it would be better to confirm wood damaging termite damage or infestation prior to destructive of the dry wall.

More specifically, upon a preliminary thermal indication of termite infestation observed with thermal imaging camera 1, detectors are positioned on the wall of the structure adjacent to the potentially infested locations in the structure 13. The detectors can be used to confirm termite infestation. These detectors include but are not limited to microwave motion detector, dogs, sound (acoustic), fiber optic scope, and gas detection and x-ray detection. A microwave motion detector can detect termite movement inside the wall cavity, however, the operator must be perfectly still while holding the device. Very often high moisture content in the wall cavity prevents an accurate measurement. Moisture content; however, can be differentiated through infrared detection. U.S. Forest Service, Mississippi. Additionally, dogs are now being used by some pest control specialists in the detection of termites. The handler/inspector is a key part of this inspection team. This individual should be a well-trained termite inspector, and also someone who can properly handle and care for the dog and become familiar with the cues and responses the dog gives when it detects an insect infestation. Truman's Scientific Guide to Pest Control Operations, $5^{th}$ Edition. Gas detectors have been marketed to aid in termite inspections. Id. X-ray detection is one of the latest pinpoint inspection techniques. X-ray detection produces a good image of termite infestation in wood structure. However, this technique requires a radioactive source and can only be employed under very strict conditions in order to contain radio active radiation. This is an active device and requires FDA and EPA approval. In addition, the equipment is quite expensive and requires extensive training.

Although the foregoing invention has been described in some detail by way of illustration and example for purposes of clarity of understanding, it will be obvious that certain changes and modifications can be made which are within the full scope of the invention.

What is claimed is:

1. A method to nondestructively confirm termite infestation in at least one site in a residential structure comprising:
   (a) using a thermal imaging camera to receive a thermal image of said residential structure to detect moisture carried by termites at an at least one site wherein said thermal image is a cold spot; and
   (b) positioning at least one detector at said at least one site to nondestructively confirm termite infestation in said at least one site in said residential structure wherein said thermal image is received without prior electromagnetic radiation of the residential structure.

2. The method of claim 1 wherein said at least one detector is a microwave motion detector.

3. The method of claim 1 wherein at least one detector is a dog.

4. The method of claim 1 wherein said at least one detector is a gas detector.

5. The method of claim 1 wherein said at least one detector is an x-ray detector.

6. The method of claim 1 further including the step of heating said structure.

7. The method of claim 1 further including the step of cooling said structure.

8. The method of claim 1 wherein said at least one detector is a fiber optic scope.

\* \* \* \* \*